United States Patent [19]

Sugier et al.

[11] 4,094,777

[45] June 13, 1978

[54] PROCESS FOR REMOVING MERCURY FROM A GAS OR A LIQUID BY ABSORPTION ON A COPPER SULFIDE CONTAINING SOLID MASS

[75] Inventors: André Sugier, Rueil Malmaison; Florentino la Villa, Nanterre, both of France

[73] Assignee: Institut Francais du Petrole, Rueil-Malmaison, France

[21] Appl. No.: 751,452

[22] Filed: Dec. 16, 1976

[30] Foreign Application Priority Data

Dec. 18, 1975 France ............................... 75 39215
Jan. 23, 1976 France ............................... 76 02079

[51] Int. Cl.$^2$ ............................................ B01D 15/06
[52] U.S. Cl. ........................................ 210/32; 55/59; 55/74; 210/36; 210/38 B

[58] Field of Search ................... 55/74, 54, 59, 61; 75/101 BE, 108, 109, 121; 210/24, 28, 30 R, 36, 38 B, 40, 42 R, 47, 32, 502, 504; 252/416; 423/100, 101

[56] References Cited

U.S. PATENT DOCUMENTS

| | | | |
|---|---|---|---|
| 3,055,824 | 9/1962 | Squires et al. ...................... | 252/416 |
| 3,510,265 | 5/1970 | Kawahata ............................ | 252/416 |
| 3,695,838 | 10/1972 | Knepper et al. .................... | 423/101 |
| 3,755,161 | 8/1973 | Yokota et al. ..................... | 210/38 B |
| 3,769,205 | 10/1973 | Williams ............................ | 210/38 B |
| 3,841,102 | 10/1974 | Cinner et al. ..................... | 210/42 R |
| 3,873,581 | 3/1975 | Fitzpatrick et al. ................ | 210/24 |
| 3,989,623 | 11/1976 | Neal ................................. | 210/38 B |

*Primary Examiner*—Charles N. Hart
*Assistant Examiner*—Ivars Cintins
*Attorney, Agent, or Firm*—Millen & White

[57] ABSTRACT

Mercury is removed from a gas or a liquid by absorption on a solid mass, which mass contains a carrier and sulfided copper.

21 Claims, No Drawings

PROCESS FOR REMOVING MERCURY FROM A GAS OR A LIQUID BY ABSORPTION ON A COPPER SULFIDE CONTAINING SOLID MASS

It is known that, depending on its origin, natural gas contains variable quantities of mercury, generally 0.1 to 50 $\mu g/m^3$ of gas. This leads on the one hand to the danger of pollution by mercury which is recognized as being a toxic element and on the other hand the danger of corrosion of certain materials in which the natural gas has to travel. It is therefore essential to provide a mercury extraction process for the treatment of natural gas. In addition to natural gas in the liquid or gaseous state, other fluids contain traces of mercury and require treatment, for example electrolytic hydrogen.

It is known that certain metals, for example gold, silver and copper form amalgams with mercury and that this property is used particularly in mercury dosing. Mercury extraction by these metals has not been used industrially on a large scale because the V. V. H. (volume of charge per volume of trapping mass and per hour) which can be used is very small with the known devices where the metal used for extraction is in mass form, particularly wires, plates, crushed material etc. Such a mass form does not provide sufficient metal area per gram of metal to permit industrial utilization inasmuch as for the treatment of large quantities of gas or liquid, the weight and cost of the extracting metal required becomes prohibitive.

According to another proposal, the extracting material can be deposited on a support, for example glass wool, nickel wool, alumina particles or ceramic material. However, the idea is to form a continuous film of this material, forming a coating on the support and eliminating the inherent adsorptive power thereof relative to, for example, water vapor. The contact surface with the atmosphere is therefore very small, and consequently so is the mercury-absorbing capacity.

Mercury extracting masses have also been described wherein the masses are formed from activated charcoal impregnated with a silver salt. The only silver salt which can be used is a complex silver thiosulphate whereas common silver salts do not give efficient and regenerable mercury absorption masses. However, such masses are unsatisfactory for the treatment of gases which contain both mercury and molecules which are easily adsorbed by activated charcoal. This is the case with natural gas which conventionally contains at least 0.1% of $C_5$ and higher hydrocarbons which are easily absorbed by the activated charcoal. Thus, the mass very rapidly loses its mercury absorption capacity. In certain cases there is a clogging of the extracting mass.

It has been found that it is possible to work at industrially acceptable V. V. H. values, that is to say in the case of gases V. V. H. values above 1,000 and preferably between 5,000 and 40,000 without observing deactivation due to the presence, for example, of $C_5$ and higher hydrocarbons by using the novel process according to the invention.

The invention relates to a process for eliminating mercury present in a gas or liquid, and substantially comprises bringing the gas or liquid into contact with an absorption mass containing copper in the sulphurized state and a support selected from among silica, alumina, silica-alumina, silicates, aluminates and silico-aluminates. (The masses can be described interchangeably as absorption, adsorption, trapping or extracting masses inasmuch as all descriptions are appropriate).

These absorption masses are both very active and relatively inexpensive. Their activity is much greater than those containing metallic copper and can be obtained more easily than the latter. Thus, to obtain copper in an active metallic form, it is necessary to reduce the copper compounds used during the preparation of the adsorption mass, and this reduction calls for temperatures of about 300° to 350° C leading to fritting of the copper and a decrease in activity.

Unlike other sulphides such as zinc sulphide whose activity is very low, copper sulphide is very active.

The most active materials are those prepared at relatively low temperature, particularly below 300° and preferably below 100° C.

According to a first method of preparation, a copper compound is mixed with a support or dispersion material, for example a compound which is subsequently able to harden such as a cement. The copper compound is, for example, a copper hydroxide or a basic copper salt, preferably one of the following compounds:

$Cu\ CO_3$, $Cu\ (OH)_2$ $2\ Cu\ CO_3$, $Cu\ (OH)_2$ 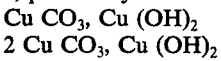

$Cu\ (OH)_2$ or one of the soluble compounds described hereinafter.

According to another method, a support is impregnated by means of a solution of a soluble compound of copper, followed by sulphurization. Examples of water-soluble compounds are copper acetate, chloride, sulphate and nitrate.

Sulphurization follows the incorporation or impregnation of the copper compound. Sulphurization temperatures below 300° C are preferred, particularly preferably they are below 100° C, for example 0°–100° C. To aid low temperature sulphurization, it is advantageous to add a small proportion of a soluble silver compound to the copper compound. This aids sulphurization and leads to a synergistic increase of the activity of the mass obtained. The weight of the silver sulphide calculated in silver is preferably between 0.05 and 5% by weight of the mass. Other metals can be present, for example iron.

The preferred supports have a specific surface area between 20 and 250 $m^2\ g^{-1}$, but these values are not limitative.

The copper sulphide weight expressed in copper represents 2 to 65% and preferably 5 to 50% of the weight of the mass. Preference is given to masses whereof at least 30%, and preferably at least 80% of the copper is in the sulphide state.

The sulphurization agent used can be a gaseous agent, for example hydrogen sulphide, or a solution of a sulphide in water or in an organic solvent, for example an aqueous solution of sodium sulphide, potassium sulphide or ammonium sulphide.

The absorption masses are preferably used in the form of a fixed bed through which can pass the liquid or gas to be purified.

It has been found that masses having an average pore diameter at least equal to 100 A have an increased stability in the presence of charges containing condensable hydrocarbons ($C_4$ or above $C_4$).

The obtention of masses (or supports for producing these masses) having an average pore diameter of at least 100 A necessitates during the production of the mass or support the incorporation of pore-forming materials such as those used in the production of macroporous catalysts.

These materials can in particular belong to the following classes:
- volatile or heat-decomposable 3 for example, cellulose or cellulose derivatives, ammonium carbonates, polymethacrylates, polystyrene, sugars, starch or gums;
- soluble materials (which can be eliminated by simply washing with water), for example sugars and ammonium carbonate;
- materials entraining air in the paste and forming bubbles, for example oleic acid, natural wood resin, fish oil, stearic acid, wetting agents, alkaline salts, sulphonated organic compounds and soaps.

The most efficient masses have a surface area of 20 to 250 m$^2$/g. The specific surface area is determined by the B. E. T. method and the diameter of the crystallites is determined either by X-ray diagrams or by electron-microscopy or on the basis of the carbon-monoxide volume chemically absorbed according to the method described by T. A. Dorling and R. L. Moss in the Journal of Catalysis, Vol. 7, 378, 1967.

The temperature range where the trapping masses are effective is generally between $-50°$ and $+200°$ C.

This trapping can be carried out at atmospheric pressure or under a higher or lower pressure, whereby the total pressure can reach, for example, 200 bars.

The V. V. H. (volume of charge per volume of trapping mass and per hour) can vary for example between 500 and 50,000, but working preferably takes place at a V. V. H. between 4,000 and 20,000 when treating a gas. In the case of liquid charges, the V. V. H. is preferably between 0.1 and 50.

The treated gases can contain, for example between 10 nanograms and 1 gram or more of mercury per cubic meter.

The mercury elimination device can comprise a single reactor or at least two reactors in parallel but preferably at least two reactors in series are used.

Considering the case of three reactors in series, A, B and C, working takes place in the following manner: when the first reactor A has reached an extraction efficiency which is only, for example, 70% of its initial efficiency the trapping mass contained is regenerated, i.e., A.

During this regeneration all the gases to be treated are passed to reactors B and C. After the regeneration of A, the gases pass into B and C and then into A.

B is then regenerated when it has reached 70% of its efficiency, and during this regeneration the gases pass into C and A.

After regeneration of B, gases pass into C and A, then B.

C is then regenerated and so on.

The regeneration can take place either in the reactor or in a unit provided for this purpose after discharging the trapping mass.

Regeneration takes place by heating with scavenging by an oxidizing, neutral or reducing gas, for example air, methane or hydrogen, preferably for 0.1 to 48 hours at a temperature of 200° to 500° C. If necessary, resulphurization takes place using the same procedure as for the initial sulphurization.

The following examples illustrate the performance of the present invention.

A. Preparation of mercury trapping masses

Masses A and B 800 g of a refractory aluminous cement of cement type Secar 250 produced by the Lafarge Company are mixed in a mixer with 280 g of precipitated copper carbonate Cu CO$_3$, Cu (OH)$_2$. The homogenized powder is treated with 150 ml of a 1% aqueous solution of methyl cellulose (methocel). The thus obtained paste is mixed for 30 minutes and then extruded into cylinders of diameter 5 mm and length 4 to 6 mm.

The extrudates are then dried for 4 hours at 80° C. After drying, half the extrudates are treated at ambient temperature with a hydrogen sulphide flow up to the completion of H$_2$S absorption, whereby mass A according to the invention is obtained. The other half is treated at 300° C with a hydrogen flow for three hours until all the copper is in a metallic state. In this way mass B is obtained (does not meet the requirements of the present invention).

Mass C 800 g of a refractory aluminous cement of cement type Secar 250 produced by the Lafarge Company are mixed in a mixer with 280 g of precipitated copper carbonate Cu CO$_3$, Cu (OH)$_2$. The homogenized powder is then placed on a dragee-making machine where dragees are made by water spraying.

The dragee-making machine is regulated in such a way that the balls produced have a diameter of 4 to 6 mm. The balls are then dried at 80° C for 4 hours and then treated with a hydrogen sulphide flow up to total sulphurization. In this way mass C according to the invention is obtained.

Mass D 800 g of a refractory aluminous cement of cement type Secar 250 produced by the Lafarge Company are mixed in a mixer with 308 g of zinc carbonate Zn CO$_3$. The homogenized powder is treated with 150 ml of an aqueous 1% methyl cellulose solution. The thus obtained paste is mixed for 30 minutes and then extruded in the form of cylinders of diameter 5 mm and length 4 to 6 mm.

The extrudates are then dried for 4 hours at 80° C and then treated with an H$_2$S flow up to complete sulphurization. The mass obtained is not according to the invention.

Masses E and F 1 kg of alumina balls of 50 m$^2$ g$^{-1}$ specific surface area and 60 ml/ 100 g porous volume is impregnated with 600 ml of an aqueous solution containing 240 g of copper nitrate Cu (NO$_3$)$_2$, 3 H$_2$O.

After drying for 4 hours at 80° C, half the balls are treated for 5 hours at ambient temperature with an H$_2$S flow thereby yielding mass E. The other half is treated for 5 hours at 280° C in a hydrogen sulphide flow, leading to mass F.

Analysis by X-ray diffraction indicates that in the case of mass E 52% of the copper is in the form of copper sulphide, and in the case of mass F all the copper is in the form of copper sulphide.

Mass G 1 kg of alumina balls identical to those used as a support in the preparation of masses E and F was impregnated with 600 ml of a solution containing 240 g of copper nitrate and 3.2 g of silver nitrate.

After drying for 4 hours at 80° C, the balls are treated under the same conditions as mass E in an $H_2S$ flow at ambient temperature for 5 hours.

Analysis by X-ray diffraction indicates that all the copper and all the silver are in the form of sulphides.

Mass H 1 kg of alumina balls identical to those used as a support in the preparation of masses E, F and G is impregnated with 600 ml of a solution containing 200 g of $CuCl_2$, $2H_2O$. After heating for 2 hours at 200° C the balls are impregnated with 580 ml of an aqueous solution containing 300 g of sodium sulphide $Na_2S$, $9H_2O$.

The balls are then washed until more than 95% of the sodium used is extracted.

The washed balls are then dried for 4 hours at 80° C giving mass H.

Analysis shows that more than 90% of the copper is in the sulphide state.

Average composition of Secar 250 cement:
$Al_2O_3$: 70%
CaO : 26%
$Na_2O$ : 0.5%
$SiO_2$ : 0.2%
Miscellaneous: 3.3%

B. Results of mercury absorption

The following procedure was used:

The apparatus comprises a metal tube whose inactivity for mercury fixing has been checked. It contains 30 ml of the adsorption mass to be tested and through which is passed a regulatable gas flow. The natural gas used has a volumetric content of $CH_4$ of 84% and of $C_5$ and higher products of 0.6%, the remainder being $N_2$, $CO_2$, $C_2H_4$, $C_3H_8$ and $C_4H_{10}$, the mercury content being 19 $\mu g/m^3$ NTP.

The mercury content was determined by using a Coleman mercury analyzer based on the method of Hatch and Ott described in Analytical Chemistry, December 1968.

The efficiency of the adsorption masses is initially evaluated at ambient temperature in the new state and at various V. V. H. values with natural gas having a mercury content of 19 $\mu g/m^3$, the composition having been given hereinbefore. The adsorption volume is 40 ml. Working takes place under a pressure of 35 bars.

The efficiency level is defined by:

$$\frac{\text{Hg content on entry} - \text{Hg content on discharge}}{\text{Hg content on entry}} \cdot 100$$

The results are given in Table I.

TABLE I

| Mass | V.V.H. | Efficiency |
|------|--------|------------|
| A    | 10,000 | 99.9       |
|      | 15,000 | 99.9       |
|      | 20,000 | 99.9       |
| B    | 10,000 | 98.5       |
|      | 15,000 | 94.2       |
|      | 20,000 | 92.1       |
| C    | 10,000 | 99.9       |
|      | 15,000 | 99.9       |
|      | 20,000 | 99.9       |
| D    | 10,000 | 96.8       |
|      | 15,000 | 92.0       |
|      | 20,000 | 71.5       |
| E    | 10,000 | 99.5       |
|      | 15,000 | 94.2       |
|      | 20,000 | 90.7       |
| F    | 10,000 | 99.9       |
|      | 15,000 | 99.5       |
|      | 20,000 | 97.2       |
| G    | 10,000 | 99.9       |
|      | 15,000 | 99.9       |
|      | 20,000 | 99.9       |
| H    | 10,000 | 99.9       |
|      | 15,000 | 99.9       |
|      | 20,000 | 99.8       |

TABLE I-continued

In order to evaluate the mercury absorption capacity of these masses, a volume of gas is passed over the masses such that at V. V. H. 5,000 the mercury quantity passed over the masses is 5% of the total weight thereof, after which an activity test is performed under the same conditions as defined hereinbefore which gives the following results.

| Mass | V.V.H. | Efficiency |
|------|--------|------------|
| A    | 10,000 | 99.9       |
|      | 15,000 | 99.9       |
|      | 20,000 | 99.9       |
| B    | 10,000 | 95.6       |
|      | 15,000 | 91.2       |
|      | 20,000 | 81.4       |
| C    | 10,000 | 99.9       |
|      | 15,000 | 99.9       |
|      | 20,000 | 99.9       |
| D    | 10,000 | 95.1       |
|      | 15,000 | 87.3       |
|      | 20,000 | 82.4       |
| E    | 10,000 | 93.4       |
|      | 15,000 | 89.2       |
|      | 20,000 | 62.4       |
| F    | 10,000 | 99.9       |
|      | 15,000 | 98.2       |
|      | 20,000 | 94.8       |
| G    | 10,000 | 99.9       |
|      | 15,000 | 99.9       |
|      | 20,000 | 99.2       |
| H    | 10,000 | 99.9       |
|      | 15,000 | 99.9       |
|      | 20,000 | 99.5       |

We claim:

1. In a process for the elimination of mercury present in a gas or liquid comprising contacting the liquid or gas with an absorption mass in a fixed bed, the improvement wherein the absorption mass consists essentially of:
   (a) a solid dispersant or support selected from the group formed by silica, alumina, silica-alumina, silicates, aluminates and silico-aluminates,
   (b) copper whereof at least 30% is in the sulphide state and wherein the copper sulphide proportion in the absorption mass, calculated as copper, represents 2 to 65% of the weight of the mass, and
   (c) 0–5% of silver in the sulfide state.

2. A process according to claim 1 in which the support is alumina.

3. A process according to claim 1, in which the absorption mass results from the mixture of a copper hydroxide or salt with said support followed by shaping and sulphurization of the latter.

4. A process according to claim 3, in which the absorption mass results from a mixture of a basic copper carbonate with said support.

5. A process according to claim 3, in which sulphurization is performed by means of hydrogen sulphide.

6. A process according to claim 3, in which sulphurization is performed with an aqueous solution of sodium sulphide followed by washing out more than 95% of the sodium.

7. A process according to claim 1, in which the absorption mass results from the impregnation of a support by means of a solution of a soluble copper compound, followed by sulphurization.

8. A process according to claim 7, in which said solution contains both a soluble copper compound and a soluble silver compound.

9. A process according to claim 7, in which sulphurization is performed with an aqueous solution of sodium sulphide followed by washing out more than 95% of the sodium.

10. A process according to claim 7, in which sulphurization is performed by means of hydrogen sulphide.

11. A process according to claim 1, in which the proportion of copper sulphide in the absorption mass, calculated as copper, represents 5 to 50% of the weight of the mass.

12. A process according to claim 1, further comprising regeneration of the absorption mass by heating the mass following a mercury absorption stage.

13. A process according to claim 12, in which the absorption mass is regenerated by heating in the presence of a light hydrocarbon.

14. A process according to claim 13, wherein steam is in mixture with said light hydrocarbon.

15. A process according to claim 1, in which a natural gas containing a major proportion of methane, a minor proportion of $C_5$ hydrocarbons and a minor proportion of mercury is treated.

16. A process according to claim 1, in which the absorption mass is activated by heating in the presence of a light hydrocarbon.

17. A process according to claim 16, wherein steam is in mixture with said light hydrocarbon.

18. A process according to claim 1, wherein the mass has an average pure diameter of at least equal to 100 A.

19. A process according to claim 1, wherein the mass has a surface area of 20–250 $m^2/g$.

20. A process according to claim 1, wherein at least 80% of the copper is in the sulfide state.

21. A process according to claim 1, wherein natural gas is treated at a rate of 4,000–20,000 V. V. H.

* * * * *